United States Patent [19]

McDonald

[11] Patent Number: 5,242,450
[45] Date of Patent: Sep. 7, 1993

[54] EYE IMPLANTABLE LENS HAPTICS TWIST APPARATUS

[75] Inventor: Henry H. McDonald, 65 N. Madison, Ste. 810, Pasadena, Calif. 91101

[73] Assignees: Henry H. McDonald; William W. Haefliger, both of Pasadena, Calif.; a part interest

[21] Appl. No.: 884,904

[22] Filed: May 18, 1992

[51] Int. Cl.⁵ ............................................. A61F 9/00
[52] U.S. Cl. ................................... 606/107; 606/205; 623/6
[58] Field of Search .................. 623/6, 4, 5; 606/107, 606/205, 206, 207, 210, 211

[56] References Cited

U.S. PATENT DOCUMENTS

| | | | |
|---|---|---|---|
| 3,882,872 | 5/1975 | Downs et al. | 606/107 |
| 4,190,049 | 2/1980 | Hager et al. | 623/4 X |
| 4,530,117 | 7/1985 | Kelman | 606/107 X |
| 4,573,998 | 3/1986 | Mazzocco | 623/6 |
| 4,759,359 | 7/1988 | Willis et al. | 623/6 X |
| 4,813,957 | 3/1989 | McDonald | 623/6 |
| 4,844,065 | 7/1989 | Faulkner | 606/107 |
| 4,888,015 | 12/1989 | Domino | 623/6 |
| 4,917,680 | 4/1990 | Poley | 623/6 |
| 4,919,130 | 4/1990 | Stoy et al. | 606/107 |
| 4,934,363 | 6/1990 | Smith et al. | 623/6 X |
| 4,957,505 | 9/1990 | McDonald | 623/6 |
| 4,959,070 | 9/1990 | McDonald | 623/6 |
| 5,047,049 | 9/1991 | Salai | 606/205 |
| 5,098,439 | 3/1992 | Hill et al. | 623/4 X |
| 5,147,369 | 9/1992 | Wagner | 606/107 |

FOREIGN PATENT DOCUMENTS

| | | | |
|---|---|---|---|
| 3305826 | 8/1984 | Fed. Rep. of Germany | 623/6 |
| 3816059 | 11/1989 | Fed. Rep. of Germany | 623/6 |

*Primary Examiner*—Randall L. Green
*Assistant Examiner*—Mary Beth O. Jones
*Attorney, Agent, or Firm*—William W. Haefliger

[57] ABSTRACT

A surgical apparatus useful for eye surgery, wherein an incision is made in the eye coroscleral tissue, and via which a plastic lens is to be introduced into an eye lens zone in a capsule from which a natural lens has been removed, the lens having haptic loop structure attached thereto, comprising a surgical forceps having two longitudinally elongated laterally spaced arms and two blades, the arms extending in parallel relation, each blade integral with an arm at the forward end thereof, each blade being blunt at the forward end thereof; whereby the forceps may be displaced to controllably receive a haptic between the blades and to controllably bend the haptic relative to the lens for positioning the haptic into the capsular "bag" or cavity, or force the haptic to be released in the sulcus, posterior to the iris, or anterior the capsule.

7 Claims, 2 Drawing Sheets

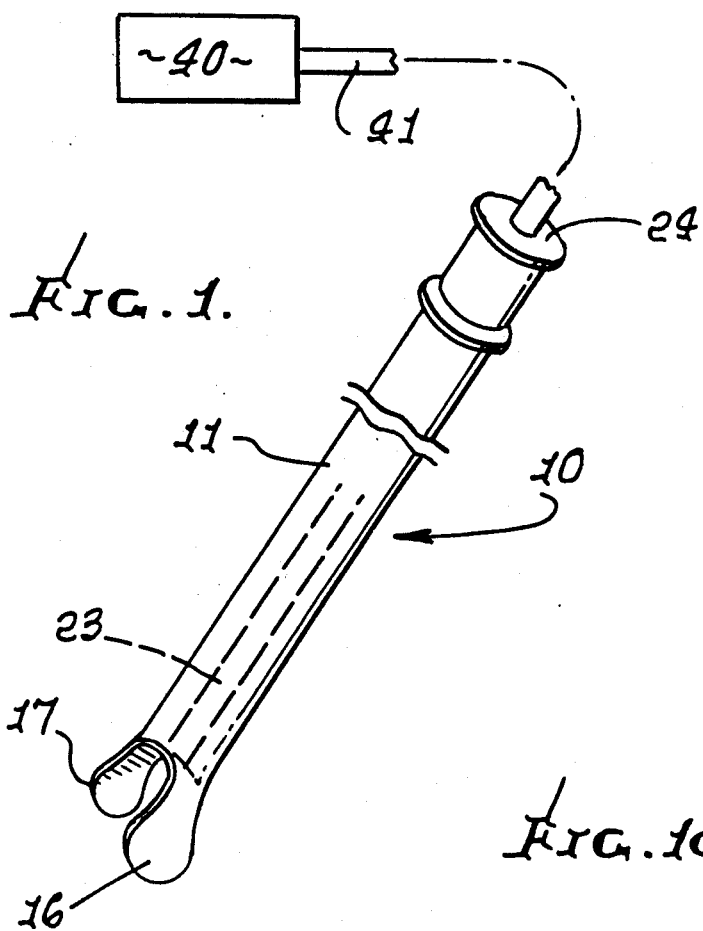
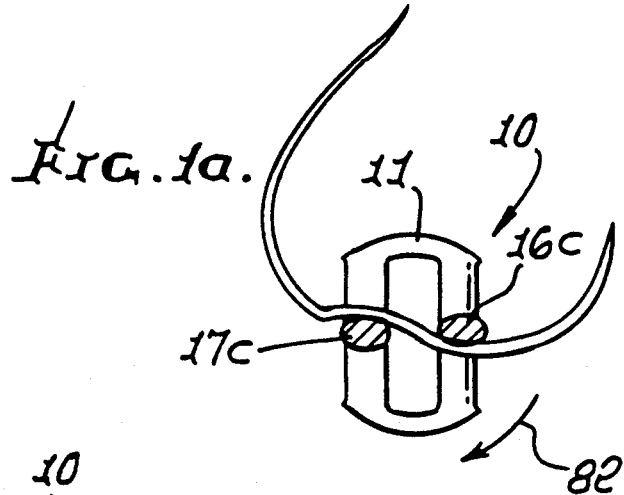
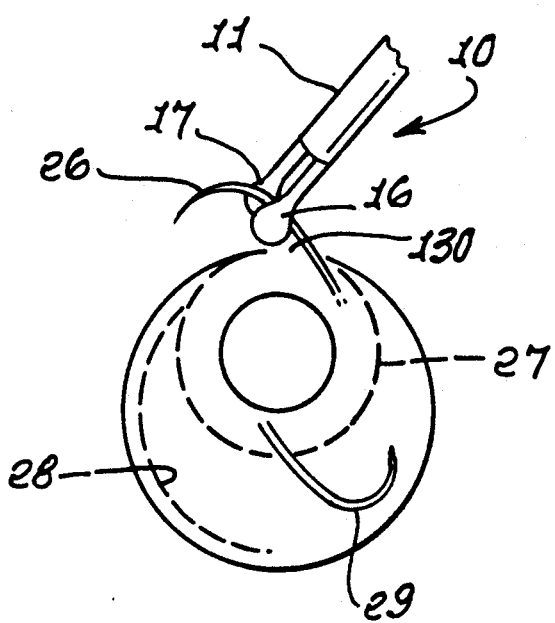

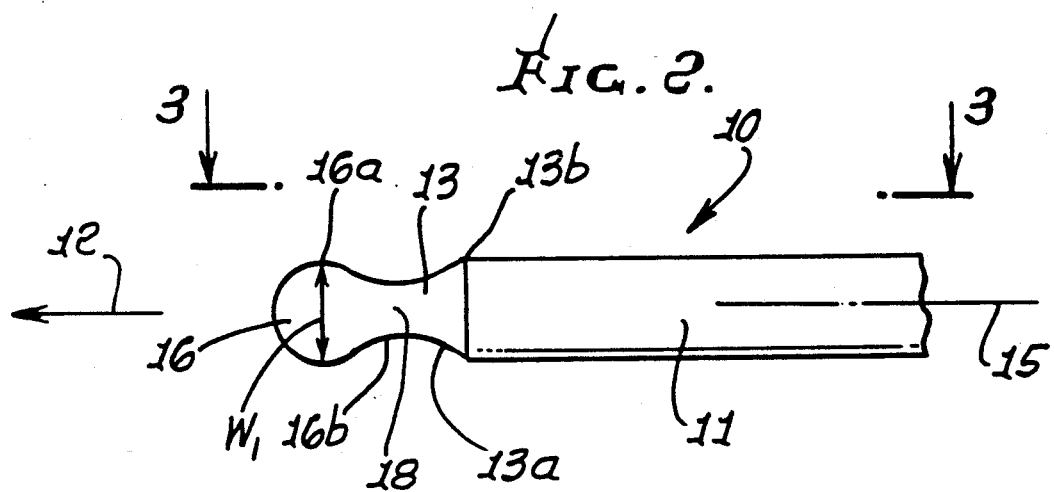
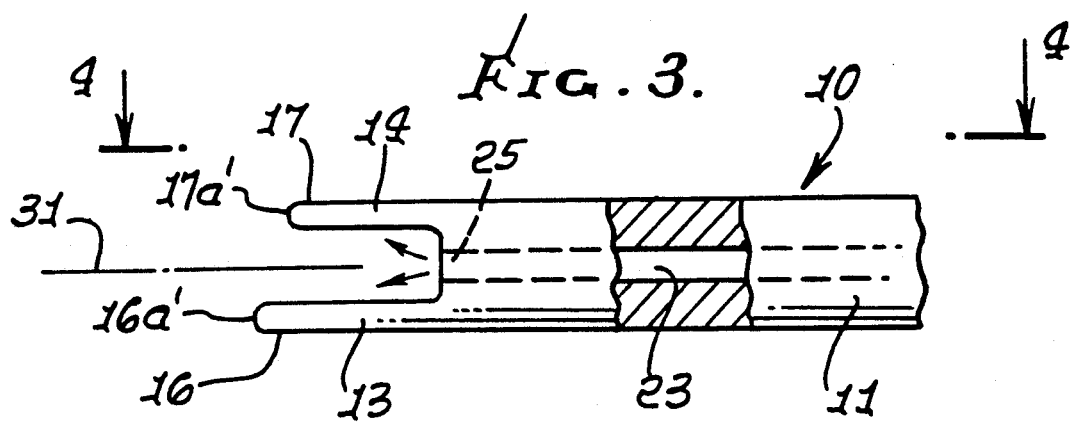
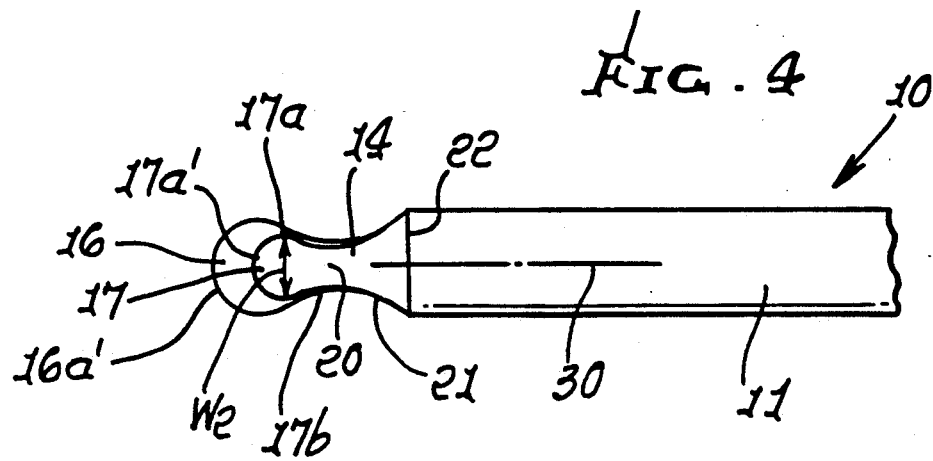

EYE IMPLANTABLE LENS HAPTICS TWIST APPARATUS

BACKGROUND OF THE INVENTION

This invention relates generally to intraocular lens implantation, and more particularly concerns apparatus and method for maneuvering haptics attached to or integral with an artificial lens during its implantation in the eye.

A common difficulty encountered during insertion of an artificial lens into the eye is that of haptic insertion. Generally speaking, two haptics are integral with or attached to or are integral with the lens to project oppositely therefrom; and it is necessary to insert both haptics into the eye cavity in a leading and trailing sequence, as respects the two haptics.

The purpose of the haptics when implanted is to position the lens correctly in the eye. Due to the very short length of the incision in the side wall of the eye, proper maneuvering of the haptics through the incision and into the eye cavity requires great skill. The problem is made more difficult when a folded, soft, silicon lens is to be implanted, since the lens tends to automatically unfold in the eye after its release by forceps, and this can occur suddenly and prior to complete insertion of the lagging or trailing haptic into the eye cavity, disturbing haptic insertion. Thus, failure to achieve the simultaneous insertion of both haptics and lens (i.e., optic) can occur using conventional instrumentation, during cataract surgery. There is, accordingly, great need for improved instrumentation to obviate or minimize this as well as other associated problems.

SUMMARY OF THE INVENTION

It is a major object of the invention to provide improved instrumentation and method for meeting or satisfying the above need. Basically, the surgical apparatus of the invention is useful for eye surgery wherein an incision is made in the eye corneoscleral tissue, and via which a plastic lens is to be introduced into an eye lens zone or capsule from which a natural lens has been removed, the lens having haptic means attached thereto.

Such apparatus comprises, in combination:

a) a surgical forceps having two longitudinally elongated, laterally spaced arms and two blades, the arms extending in parallel relation, each blade integral with an arm at the forward end thereof, each blade being blunt at the forward end thereof, b) whereby the forceps may be displaced to controllably receive a haptic between the blades and to controllably bend the haptic relative to the lens, for grasping the haptic, positioning the haptic in the capsule, and releasing same in the eye.

Typically, the forward edge of each blade is bi-directionally forwardly convex, i.e., convex in two planes, as will be described. This assures blade tip bluntness to prevent injury to intraocular tissue. The two blades are located at the distal end of the forceps instrument and can envelop and grasp a haptic by rotation of the elongated instrument.

Overt distortion of the haptic can occur with upon rotation of the blades, for diverting and steering the haptic into a desired location or locations, such as posteriorly into the sulcus (behind the iris and in front of the lens capsule); or even more posteriorly into the lens capsule "bag" (between the anterior lens capsule and posterior lens capsule). The blades typically have indentations on their sides which help to capture or grasp the haptic during instrument rotation, so that the blades do not force the haptic away from the grasp of the forceps.

As respects blade tip convexity in two planes a first such plane extends axially of the instrument and generally normal to the blades to bisect them; and a second axial plane extends normal to the first plane to bisect the space between the blades, whereby:

i) each blade forward end is forwardly convex in planes parallel to said first plane and intersecting said forward end, and ii) each blade forward end is forwardly convex in planes parallel to said second plane and intersecting said forward end.

Also, each blade typically has overall width substantially greater than its thickness.

As respects the provision of indentations on each blade, the blade width may smoothly narrow rearwardly of the blade maximum width zone, all edges of the projected blading being convex or rounded to prevent injury to eye tissue. One blade typically projects forwardly beyond the other, to allow its insertion through the eye slit prior to travel of the shorter blade and grasped haptic through the slit. Also, one blade extends further than the other to allow the shorter blade not to obscure the tip position of the longer blade, enabling accurate placement before rotation of the twister instrument.

It is a further object of the invention to provide the improved forceps with an irrigation cannula extending toward the space between the blades, the cannula having a discharge opening facing that space. The forceps itself may have a generally tubular body to provide the irrigation cannula, and the blades project forwardly from that tubular body.

These and other objects and advantages of the invention, as well as the details of an illustrative embodiment, will be more fully understood from the following specification and drawings, in which:

DRAWING DESCRIPTION

FIG. 1 is a perspective view of an instrument embodying the invention;

FIG. 1a is an enlarged fragmentary section showing haptic strand capture by twisting blades;

FIG. 2 is a side view of the instrument;

FIG. 3 is a side view of the instrument taken on lines 3—3 of FIG. 2;

FIG. 4 is a side view of the instrument taken on lines 4—4 of FIG. 3; and

FIG. 5 is a front view of an eye iris and pupil, with a folded lens being implanted, the lens having become unfolded and the trailing haptic being maneuvered into the eye cavity by the instrument of the invention.

DETAILED DESCRIPTION

In FIGS. 1-4, the surgical forceps 10 has a body 11, which is elongated in the direction 12, the body typically being tubular. The forceps has two longitudinally elongated and laterally spaced arms 13 and 14 which project forwardly from the body and at opposite sides of the body axis 15. These arms extend in generally parallel relation; and arm 14 may be slightly shorter than arm 13 to allow for enhanced capability for grasping and maneuvering of a haptic (typically a trailing haptic as respects insertion into the eye), by blades carried by the arms, to enable clear viewing of the position of the longer blade (arm) without its being obscured by the shorter blade (arm), and to allow sequential entry of the blades into the eye via a small slit in the sclera.

Such blades are indicated at 16 and 17 integral with the forward ends of two arms; and they are generally spoon-shaped in outline, as is clear from FIG. 2 and also from FIG. 4. In those FIGS. 2 and 4, each blade is seen to have a width which varies along the length of the blade. Thus, the width $w_1$ of blade 16 increases from the blade tip to a maximum at 16a, and then decreases rearwardly to a minimum at 16b, the blade then joining the arm at region 18, with the arm width increasing at 13a toward juncture with the tube 11 at 13b. In similar fashion, shorter blade 17 has width $w_2$, which increases toward a maximum at 17a and then decreases rearwardly to a minimum at 17b. The blade and arm 14 juncture at 20, with arm 14 width then increasing rearwardly along concave edges 21 to merge with the tube 11 at points 22.

In FIG. 4, it is clear that blade 16 projects forwardly to greater extent than blade 17, the latter being slightly smaller in outline than blade 16, enhancing the haptic maneuvering functions and capability of the two blades, and also enabling one blade to precede the other into the narrow slit in the sclera.

The body 11 provides a cannula 23, which is elongated from the rearward end of the instrument 24 and which discharges openly at 25 between the two arms 13 and 14, whereby liquid, such as a saline aqueous solution, may be supplied during surgery to discharge onto and into the eye to prevent collapse of the eye "bag" during haptic and lens insertion maneuvering, as referred to. See saline solution supply at 40 and duct 41.

In FIG. 5 and FIG. 1a, the instrument 10 is shown with the two blades on blade arms, grasping the trailing haptic trailing portion 26, which is shown projecting outwardly from the eye during insertion. The lobe-shaped blades have been positioned beyond the haptic strand so that the strand is between the narrowed blade portions 16c and 17c. See FIG. 1a. The instrument is then twisted or rotated about its axis 15 (as in direction 82 in FIG. 1a) to "capture" the haptic strand between the narrowed portions of the blades, as also indicated in FIG. 1 and also in FIG. 1a. The direction of twist is shown at 82 in FIG. 1a.

In addition, the narrowing of the blade arm extents between which the haptic is captured locates the captured haptic lengthwise of the instrument to prevent it from sliding endwise off the instrument so long as the instrument is twisted, as described. This then enables the surgeon to implant the trailing haptic into the eye cavity via the narrow slit in the wall of the eye, as referred to. See in this regard the slit 130 shown in FIG. 5, lens 27 that has passed through the slit into the eye bag 28, and opened (if folded) and the leading haptic 29 in the eye. Bi-directional bluntness or convexity of blade edges assures that eye tissue will not be damaged by push contact with the blades during haptic twisting and insertion via the slit into the eye.

As regards blade bi-directional edge convexity, note a first axial plane 30 extending generally normal to the blades in FIG. 4, and a second axial plane 31 extending generally normal to plane 30 and bisecting the space (see FIG. 2). Having such planes defined, the following convexities exist:

i) each blade forward end (see ends 16a' and 17a') is forwardly convex in planes parallel to the first plane 30 (see convexities at ends 16a' and 17a' in FIG. 3), and p0 ii) each blade forward end is forwardly convex in planes parallel to the second plane 31 and intersecting the blade forward end (see convexities at ends 16a' and 17a' in FIG. 4).

Also, each blade has overall width substantially greater than the blade thickness, as is clear from FIGS. 3 and 4.

The method of maneuvering a lens haptic into desired position in the eye includes the steps:

a) providing bladed means, b) causing the bladed means to grasp the haptic by twisting the blade means to effect bending of the haptic adjacent the bladed means, c) and maneuvering the grasped haptic into desired position in the eye.

That method also includes irrigating the grasped haptic during said maneuvering.

Haptic release after complete positioning includes reverse twisting of the blade means, and withdrawal of the blade means from the eye, via the slit in the sclera. That slit is typically between 3 and 6 millimeters length, so that the overall diameter of the instrument 10 is typically between 3 and 6 millimeters.

The instrument is also usable to force the haptic to be released in the sulcus, posterior to the iris; and to grasp a displaced (luxated or sub-luxated) haptic lens optic which has inadvertently fallen into the depths of the eye, for retrieval without severe damage to the intraocular tissues and positioning of the haptic lens optic for a very satisfactory introcapsular implantation.

I claim:

1. Surgical apparatus useful for eye surgery, wherein an incision is made in the eye coroscleral tissue, and via which a plastic lens is to be introduced into any eye lens zone in a capsule from which a natural lens has been removed, the lens having haptic loop means attached thereto, the combination comprising:

a) a surgical forceps having two longitudinally elongated, laterally spaced arms and two blades, said arms extending in parallel relation, each blade having integral connection with one of said arms at a forward end of said arm, each blade being blunt at a forward end of said blade, b) whereby the forceps may be displaced to controllably receive a haptic between the blades and to controllably bend the haptic relative to the lens for positioning the haptic in said capsule, c) each blade having width and thickness, the forceps defining a longitudinally forwardly extending axis located midway between the blades, there being a first axial plane extending generally normal to said blades and widthwise bisecting the blades, and there being a second axial plane extending normal to said first plane and bisecting the space between the blades, and i) each blade forward end being forwardly convex in planes parallel to said first plane and intersecting said blade forward end, and ii) each blade forward end being forwardly convex in planes parallel to said second plane and intersecting said blade forward end, the blade width narrowing rearwardly of said blade forward end, each blade being widthwise oppositely convex in outline in planes parallel to said second plane, d) the forceps having a generally tubular body from which said arms project forwardly, said tubular body forming an irrigation cannula extending toward the space between the blades, the cannula having a discharge opening facing said space.

2. The combination of claim 1 wherein each blade had overall width substantially greater than said blade thickness.

3. The combination of claim 1 wherein one of said blades projects forwardly to a greater extent than the other blade.

4. The method of maneuvering a lens haptic into desired position in the eye, that includes:
   a) providing bladed means,
   b) causing said bladed means to grasp the haptic by twisting said blade means to effect bending of the haptic adjacent said bladed means,
   c) maneuvering said grasped haptic into desired position in the eye,
   d) said bladed means provided to form:
      $x_1$ a surgical forceps having two longitudinally elongated, laterally spaced arms and two blades, said arms extending in parallel relation, each blade having integral connection with one of said arms a forward end of said arm, each blade being blunt at a forward end of said blade,
      $x_2$ whereby the forceps may be displaced to controllably receive a haptic between the blades and to controllably bend the haptic relative to the lens for positioning the haptic in said capsule,
      $x_3$ each blade having width and thickness, the forceps defining a longitudinally forwardly extending axis located midway between the blades, there being a first axial plane extending generally normal to said blades and widthwise bisecting the blades, and there being a second axial plane extending normal to said first plane and bisecting the space between the blades, and
      i) each blade forward end being forwardly convex in planes parallel to said first plane and intersecting said blade forward end, and
      ii) each blade forward end being forwardly convex in planes parallel to said second plane and intersecting said blade forward end, the blade width narrowing rearwardly of said blade forward end, each blade being widthwise oppositely convex in outline in planes parallel to said second plane,
   e) and said forceps provided to have a generally tubular body from which said arms project forwardly, said body formed to provide an irrigation cannula extending toward the space between the blades, the cannula formed to have a discharge opening facing said space, and irrigating said grasped haptic during said maneuvering.

5. The method of claim 4 including releasing the grasped haptic in the eye by reverse twisting of said blade means.

6. The method of claim 4 wherein the bladed means includes two blunt blades, and said maneuvering includes displacing said blunt blades through a slit in the eye wall.

7. The method of claim 4 wherein said maneuvering includes displacing one blunt blade into the slit before displacing the other blade and grasped haptic into and through the slit, into the eye.

* * * * *